United States Patent [19]
Kleiner

[11] Patent Number: 5,391,798
[45] Date of Patent: Feb. 21, 1995

[54] PROCESS FOR PREPARING 6-CHLORO-(6H)-DIBENZ [C,-E][1,2]-OXAPHOSPHORIN

[75] Inventor: Hans-Jerg Kleiner, Kronberg/Ts, Germany

[73] Assignee: Hoechst Aktiengesellschaft, Frankfurt am Main, Germany

[21] Appl. No.: 103,969

[22] Filed: Aug. 9, 1993

[30] Foreign Application Priority Data

Aug. 11, 1992 [DE] Germany .............. 4226554

[51] Int. Cl.⁶ .......................... C07F 9/6574
[52] U.S. Cl. .......................... 558/82
[58] Field of Search .................. 558/82

[56] References Cited

U.S. PATENT DOCUMENTS 3,702,878 11/1972 Saito .
4,086,206 4/1978 Saito et al. .

FOREIGN PATENT DOCUMENTS 2034887 1/1972 Germany .
2730371 1/1981 Germany .

OTHER PUBLICATIONS

Pastor, S. D., et al, *Phosphorus and Sulfur* 31:71–76 (1987).

*Primary Examiner*—Mary C. Lee
*Assistant Examiner*—Michael G. Ambrose
*Attorney, Agent, or Firm*—Connolly and Hutz

[57] ABSTRACT

Process for preparing 6-chloro-(6H)-dibenz[c,e][1,2]oxaphosphorin of the formula (I),

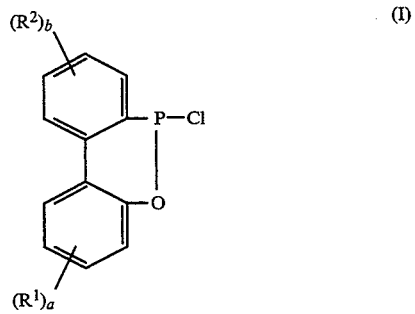

in which $R^1$ and $R^2$ are identical or different and are halogen, alkyl or alkoxy, each having from 1 to 6 carbon atoms, and a and b are integers from 0 to 3, preferably from 0 to 2, by reaction of o-phenylphenol of the formula (II),

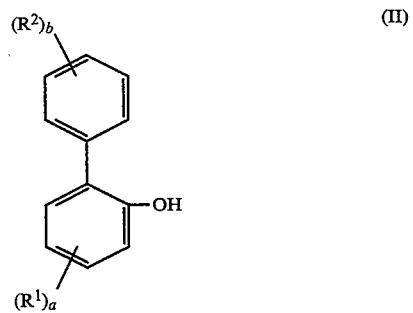

in which $R^1$, $R^2$, a and b are as defined above, with phosphorus trichloride in the presence of Lewis acids as catalysts with elimination of hydrogen chloride, wherein the phosphorus trichloride is metered into the mixture of compound (II) and Lewis acid at temperatures of 170°–220° C.

17 Claims, No Drawings

PROCESS FOR PREPARING 6-CHLORO-(6H)-DIBENZ [C,-E][1,2]-OXAPHOSPHORIN

6-Chloro-(6H)-dibenz[c,e][1,2]oxaphosphorin is an industrially significant intermediate for the preparation of flame retardants, additives for polymerization processes, photoinitiators, stabilizers for polymers and photographic material. It is generally prepared from o-phenylphenol and phosphorus trichloride in the presence of small quantities of a catalyst such as zinc chloride (DE-A 2034887). In this preparation process o-phenylphenol is slowly heated with phosphorus trichloride, in a molar ratio of about 1:1.25, to about 140°–150° C. A catalytic quantity of zinc chloride is then added and heating is resumed to a final temperature of 190°–210° C. Excess phosphorus trichloride distills off throughout the process. After purification by distillation the yield is about 80% of theoretical (in this respect see also S. D. Pastor et al., Phosphorus and Sulfur 31, 71, 1987).

In a variant of this preparation process zinc chloride is immediately added to the o-phenylphenol and the phosphorus trichloride is subsequently metered into this mixture at 80° C. Then, after completion of the phosphorus trichloride addition, the temperature is raised to 180° C. and further phosphorus trichloride is added at such a rate that slow reflux of the phosphorus trichloride is maintained (DE-A 2 730 371).

Both processes require specific temperature control. A disadvantage here is that during the stepwise increases in temperature phosphorus trichloride distills off continually and must be fed back to the process.

The invention relates to a process for preparing 6-chloro-(6H)-dibenz[c,e][1,2]oxaphosphorin of the formula (I)

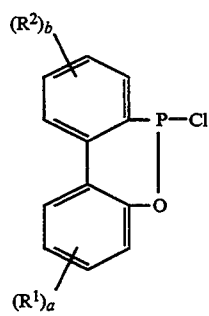

in which

R$^1$ and R$^2$ are identical or different and are halogen, preferably chlorine, alkyl or alkoxy, each having from 1 to 6, preferably from 1 to 4, carbon atoms, and a and b are integers from 0 to 3, preferably from 0 to 2, by reaction of o-phenylphenol of the formula (II)

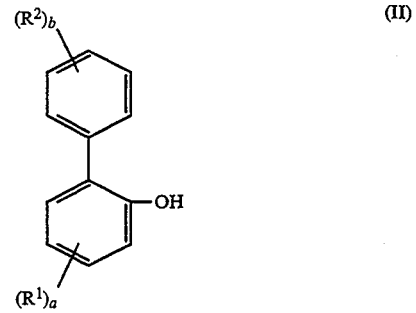

in which R$^1$, R$^2$, a and b are as defined above, with phosphorus trichloride in the presence of Lewis acids as catalysts with elimination of hydrogen chloride, wherein the phosphorus trichloride is metered into the mixture of compound (II) and Lewis acid at temperatures of 170°–220° C.

Examples of alkyl or alkoxy in the radicals R$^1$ and R$^2$ in the compounds (I)/(II) are methyl, ethyl, propyl, isopropyl and the various butyl radicals, or methoxy and ethoxy. The indices a and b in the formulae (I)/(II) are preferably the same and in particular are zero.

The process according to the invention, which proceeds in two phases with different reaction rates, is preferably carried out at temperatures of from 175° to 195° C. The reaction time is in general from 8 to 20 hours, preferably from 10 to 15 hours.

Possible catalysts are according to the invention Lewis acids, for example halides of groups IIb and IIIa of the Periodic Table, zinc chloride being particularly preferred. Further suitable catalysts are described in, for example, the abovementioned DE-A 2 034 887. Suitable amounts of catalyst are from 0.05 to 2% by weight, preferably from 0.3 to 0.6% by weight, based on the compound (II) used.

The compound (II), preferably unsubstituted o-phenylphenol, and the phosphorus trichloride are, as a rule, used in a molar ratio of at least 1:1, although a small excess of phosphorus trichloride is in general favorable. This molar ratio is preferably from 1:1 to 1:3, in particular from 1:1 to 1:2.

As already mentioned above, the reaction according to the invention proceeds in two phases with different reaction rates. The first half of the phosphorus trichloride reacts quickly and can therefore, at the given reaction temperatures, be metered in quickly. The second half of the phosphorus trichloride then reacts distinctly more slowly in the secondary reaction and must therefore be added correspondingly more slowly. This is because too rapid an addition of phosphorus trichloride forces a drop in the reaction temperature through excessive refluxing. It is advantageous, at the end of the reaction, to maintain the reaction temperature at reflux by means of excess phosphorus trichloride for a further one to six hours, preferably from 2 to 4 hours, to complete the reaction as far as possible. After the end of the reaction the excess phosphorus trichloride is distilled off, if desired in vacuo.

The process according to the invention can be carried out batchwise or continuously. The reaction of the compound (II) with the phosphorus trichloride is usually carried out under atmospheric pressure, although increased pressure is also possible. In this case the hydrogen chloride produced must be removed with pressure equalization.

The raw product (I) obtained is pure enough for numerous reactions and can be directly processed further, for example as a 50% strength solution in toluene or xylene. It is preferably used for the purposes mentioned in the introduction.

The examples below serve to illustrate the invention.

EXAMPLE 1

102 g (0.6 mol) of o-phenylphenol and 0.6 g of zinc chloride are heated to 180° C. with stirring. 82.5 g (0.6 mol) of phosphorus trichloride are then added dropwise so as to give a slow reflux of phosphorus trichloride with simultaneous evolution of hydrogen chloride. After 90 minutes about half has been added. The second half is added dropwise over about 5 hours. A further 20 g (0.146 mol) of phosphorus trichloride are added dropwise over 4 hours, since some of the phosphorus trichloride has escaped together with the hydrogen chloride and has condensed in a cold trap positioned after the apparatus. The excess phosphorus trichloride is subsequently distilled off and the 6-chloro-(6H)-dibenz[-c,e][1,2]oxaphosphorin is distilled at 0.17 kPa and goes over at a temperature of 165° C. 135 g of crystalline product are obtained, corresponding to a yield of 96% of theoretical.

EXAMPLE 2

700 g (4.12 mol) of o-phenylphenol and 4.1 g of zinc chloride are heated to 180° C. with stirring. 692 g (5.03 mol) of phosphorus trichloride are then added dropwise over 12 hours. Reflux is maintained for a further 5 hours; at the end no further hydrogen chloride is evolved. The excess phosphorus trichloride is distilled off at 120° C. in vacuo, the reaction product is cooled to 100° C. and 966 g of toluene are added. Cooling to room temperature gives a 50% strength solution of 6-chloro-(6H)-dibenz[c,e][1,2]oxaphosphorin in toluene. The $^{31}$P-NMR spectrum indicates a purity of 95.5%.

What is claimed is:

1. A process for preparing 6-chloro-(6H)-dibenz[-c,e][1,2]oxaphosphorin of the formula (I),

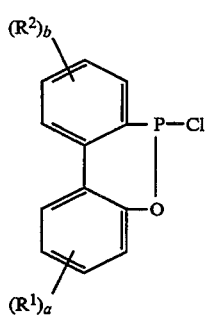

in which $R^1$ and $R^2$ are identical or different and are halogen; alkyl or alkoxy, each having from 1 to 6 carbon atoms; and a and b are integers from 0 to 3; by reaction of o-phenylphenol of the formula (II),

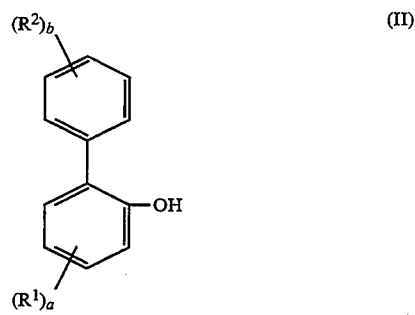

in which $R^1$, $R^2$, a and b are as defined above, with phosphorus trichloride in the presence of Lewis acids as catalysts with elimination of hydrogen chloride, wherein the phosphorus trichloride is metered into the mixture of compound (II) and Lewis acid at temperatures of 170°–220° C.

2. The process as claimed in claim 1, wherein the temperature is 175° to 195° C.

3. The process as claimed in claim 1, wherein zinc chloride is used as catalyst.

4. The process as claimed in claim 1, wherein the amount of catalyst is from 0.05 to 2% by weight, based on the compound (II).

5. The process as claimed in claim 1, wherein the compound (II) and phosphorus trichloride are used in a molar ratio of from 1:1 to 1:2.

6. The process as claimed in claim 1, wherein a and b in the formulae (I) or (II) are zero.

7. A process for preparing 6-chloro-(6H)-dibenz[-c,e][1,2]oxaphosphorin of the formula (I′),

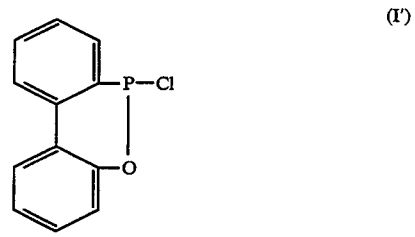

by reaction of o-phenylphenol of the formula (II′),

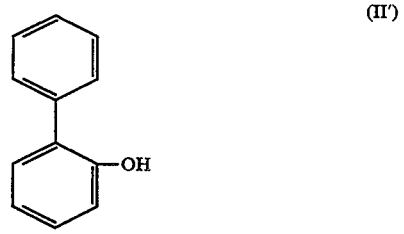

with phosphorus trichloride in the presence of from 0.05 to 2% by weight, based on o-phenylphenol (II), of zinc chloride as catalyst with elimination of hydrogen chloride, wherein the phosphorus trichloride is metered into the mixture of o-phenylphenol and zinc chloride at temperatures of 170°–220° C.

8. The process as claimed in claim 7, wherein the o-phenylphenol (II) and the phosphorus trichloride are used in a molar ratio of from 1:1 to 1:2.

9. The process as claimed in claim 1, wherein a and b in formula (I) are from 0 to 2.

10. The process as claimed in claim 1, wherein a and b in the formulae (I) and (II) are zero.

11. The process as claimed in claim 1, wherein $R^1$ and $R^2$ are identical or different and are chlorine, alkyl or alkoxy having from 1 to 4 carbon atoms.

12. The process as claimed in claim 1, wherein the reaction is carried out from 8 to 20 hours.

13. The process as claimed in claim 11, wherein the reaction is carried out from 10 to 15 hours.

14. The process as claimed in claim 13, wherein the amount of catalyst is from 0.3 to 2% by weight, based on the compound (II).

15. The process as claimed in claim 13, wherein the amount of catalyst is from 0.3 to 0.6% by weight, based on the compound (II).

16. The process as claimed in claim 1, wherein the compound (II) and phosphorus trichloride are used in a molar ratio of at least 1:1.

17. The process as claimed in claim 1, wherein the compound (II) and phosphorus trichloride are used in a molar ratio of from 1:1 to 1:3.

* * * * *